United States Patent [19]

Magri

[11] 4,114,441

[45] Sep. 19, 1978

[54] METHOD AND APPARATUS FOR MEASURING THE HEIGHT OF FILLING MATERIAL ON A SURFACE, SUCH AS WITHIN A CONTAINER

[75] Inventor: Antonio Magri, Milan, Italy

[73] Assignee: G. H. Endress & Co., Switzerland

[21] Appl. No.: 799,517

[22] Filed: May 23, 1977

[30] Foreign Application Priority Data

Jun. 9, 1976 [CH] Switzerland .......................... 7228/76

[51] Int. Cl.² ............................................. G01F 23/28
[52] U.S. Cl. .................................... 73/290 V; 73/629
[58] Field of Search ................... 73/290 V, 67.9, 67.7, 73/67.6, 627, 629; 340/1 L, 1 C

[56] References Cited

U.S. PATENT DOCUMENTS

| | | | |
|---|---|---|---|
| 2,775,748 | 12/1956 | Rod et al. ....................... | 73/290 V X |
| 3,223,964 | 12/1965 | Stadlin ............................ | 73/290 V X |
| 3,985,030 | 10/1976 | Charlton ......................... | 73/290 V |
| 4,000,650 | 1/1977 | Snyder ............................ | 73/290 V |

Primary Examiner—Charles A. Ruehl

[57] ABSTRACT

A method of measuring a filling level in a container or the height of loose material over a storage surface, comprises transmitting and recording a sound pulse having a duration at least as long as a pulse which travels to the lowermost level of the material, recording the echo of the sound pulse from the actual material filling level, and measuring, as a measure of the filling level, the time interval between the end of the transmitted pulse and the end of the echo pulse. A device for measuring the height of the filling material on a surface, comprises an electroacoustic transmitting transducer excited by an electric pulse generator and having a receiving transducer whose output is connected to an electrical time measuring device. The transmitting transducer and the receiving transducer are mounted over the surface of the material being added thereon and a control circuit of the measuring device is adjusted so that it starts measuring the time at the end of the transmitted pulse and stops at the end of the echo pulse.

13 Claims, 3 Drawing Figures

METHOD AND APPARATUS FOR MEASURING THE HEIGHT OF FILLING MATERIAL ON A SURFACE, SUCH AS WITHIN A CONTAINER

FIELD AND BACKGROUND OF THE INVENTION

This invention relates in general to methods and apparatus for measuring the height of fill of material and, in particular, to a new and useful device for measuring the height of filling material on a receiving surface.

DESCRIPTION OF THE PRIOR ART

The invention concerns a method of measuring the level of filling in a container or the height of loose material on a storage place, using the echo-sounding principle, by measuring the total time of transit of a sound pulse or ultrasonic pulse directed onto the surface of the filling material or loose material, and of the echo pulse reflected from the surface of the filling material or loose material, and it also concerns an arrangement for carrying out the said method.

It is known that such echo-sounding measuring methods are used for measuring the filling level in open and closed containers, and for measuring the height of loose material on storage places. For the sake of simplicity, in what follows by way of example, reference will always be made to the measurement of filling height in a container.

Known methods of this kind are usually carried out with arrangements comprising an electroacoustic transmitting transducer, excited by an electric pulse generator, and an acoustic-electric receiving transducer connected to an electronic time-measuring device, the transmitting transducer and receiving transducer being mounted above the filling material in the container. The transmitting transducer and receiving transducer may also be the same transducer. The transmitting transducer transmits a sound pulse or ultrasonic pulse, the duration of which is as short as possible compared with the shortest total transit time occurring (corresponding to the maximum level of filling in the container). The transmitted pulse strikes the surface of the filled material, of which pulse a fraction of the transmitted energy is reflected as echo pulse, which returns to the receiving transducer. A time-measuring device measures the time interval between the commencement of transmission of the transmitted pulse and the commencement of reception of the echo pulse. This time interval corresponds to the total transit time of the pulse from the transmitting transducer to the surface of the material in the container and back to the receiving transducer, and is a measure of the distance travelled by the pulse, since the speed of sound is known. If the two transducers are at the same height (or are combined in a single transducer), this total distance is equal to double the distance between the transducers and the surface of the filled material. Since, on the other hand, the distance of the transducers from the bottom of the container is known, the level of filling in the container can be calculated from that distance.

In these known methods and arrangements, there is a considerable risk of faulty measurements if interfering pulses can occur in the container, which pulses reach the receiving transducer and are evaluated by the latter as echo pulses. If, after the transmission of a transmission pulse, such an interference pulse arrives at the receiving transducer before the correct echo signal arrives, the time interval measured will be too short and, consequently, too high a level of filling will be indicated. The danger of the occurrence of such interference pulses is particularly great if measurement of the filling level is carried out during filling or emptying of the container. This in particular is necessary for the control of automatic filling and emptying processes for terminating filling on reaching a predetermined maximum filling level, or during emptying to restart filling on reaching a predetermined minimum filling level. In these operations, there usually occurs a considerable noise level which may cause interfering pulses leading to the previously mentioned wrong measurement. Since the wrong measurement always indicates too high a level of filling, the result is that charging of the container is ended prematurely before the desired maximum filling level is reached, or that on emptying, charging cannot be restarted, although the level has already fallen below the permissible filling level.

The probability of the occurrence of disturbing pulses at the receiving transducer is obviously all the greater, the greater is the length of time between the transmitted pulse and the received pulse, and the lower therefore is the filling level. On the other hand, however, the noise level produced in the filling process is also greater, the lower the filling level, because the material being charged has a greater height of fall. Accordingly, there is a greater risk of wrong measurements at a low filling level resulting in the indication of a filling level which is too high.

This phenomenon is all the more strongly effective, the greater the height of the container. The fraction of the transmitted energy arriving at the receiving transducer is in fact smaller, the greater is the distance travelled by the transmitted pulse and echo pulse. The sensitivity of the receiving transducer and the circuits connected to it must be so dimensioned that, for the maximum transit time occurring, i.e., for the lowest occurring filling level, the echo pulse can still be evaluated with certainty. However, the greater this sensitivity, the greater also is the danger of response to disturbing pulses. In order to avoid excessive sensitivity on the receiving side, the maximum possible pulse energy is applied on the transmitting side. Due to the short duration of the transmitted pulses, this means that they have a high energy density per unit time. The transmission of sound pulses of high energy density in its turn calls for considerable expenditure on the transmitting side.

SUMMARY OF THE INVENTION

The present invention provides a method and an arrangement for measuring the filling level in a container, or the charged material height at storage places, using the echo-sounding principle, in which the risk of wrong measurements due to disturbing pulses caused by the noise level is largely precluded, and the measurement can be carried out with relatively low energy density of the transmitted pulses.

In the method, according to the invention, a sound pulse or supersonic pulse is transmitted and received whose duration is at least equal to the total transit time corresponding to the lowest filling level occurring, and as a measure of the filling level, the time interval between the end of the transmitted pulse and the end of the echo pulse is measured.

In the method of the invention, comparatively long pulses are used whose duration is so long that even with the maximum total transit time occurring, i.e., the lowest filling level occurring, reception of the echo pulses begins before the transmission of the transmitted pulse ends. The echo pulse has the same duration as the transmitted pulse, but arrives at the receiving transducer with a time lag corresponding to the total transit time to be measured. Consequently, the time interval between the end of the transmitted pulse and the end of the echo pulse is also equal to the total transit time forming a measure of the level of filling in the container or of the loose material level at the storage place. In the method according to the invention, this time interval is measured in which the echo pulse continues after the end of the transmitted pulse.

It will be readily apparent that interference pulses occurring during the transmission of the transmitted pulse have no influence on the measurement, since no time measurement occurs during that time. However, even interference pulses, occurring during time measurement cannot falsify the time measurement, since these interference pulses are then superimposed on the still existent echo pulse, but cannot mask the end of the echo pulse which alone determines the end of the time measurement. Thus, incorrect measurements caused by interference pulses are almost entirely excluded, and the method is more particularly suitable for making filling level measurements in cases of considerable noise levels such as occurs particularly during the filling and emptying of a container.

In consequence of the insensitivity with respect to interference pulses, it is possible to operate with substantially lower energy levels. Furthermore, since the pulse energy is distributed over a much greater pulse duration, the transmitted pulses have a much smaller energy density. The transmission of pulses of longer duration with comparatively smaller energy density is possible by means of much simpler and cheaper devices than the transmission of very short pulses of greater energy density.

A particular advantage of the method, according to the invention, consists in that the comparatively long transmitted pulse can be modulated in a simple manner. If the receiving side device used for evaluating the echo pulse is so constructed that it responds selectively to the modulation, there is obtained an additional possibility of eliminating unwanted interference signals.

Finally, the arrangement used for carrying out the method can be readily adapted to containers or storage places of very different heights. For this purpose, it is only necessary to adjust the duration of the transmitted pulse corresponding to the distance between the transducers and the bottom of the container or storage place. In contrast thereto, in the known methods which operate with short pulses for differences in height of about 10 to 15 meters, different transducers must be employed in each case and must be tuned correspondingly.

An arrangement for carrying out the method of the invention comprises, in the usual manner, an electroacoustic transmitting transducer excited by an electric pulse generator, and an acoustic-electric receiving transducer, whose output is connected to an electronic time measuring device, the transmitting transducer and the receiving transducer being mounted above the filled material in the container or above the loose material at the storage places, and the arrangement is characterized according to the invention in that a control circuit is provided, which sets the time measuring device in motion at the end of the transmitted pulse and stops it at the end of the echo pulse.

Accordingly, it is an object of the invention to provide a method for measuring the height of filling material on a surface which receives the material, which comprises transmitting and recording a sound pulse having a duration at least as long as the pulse to travel to the lowermost level of the material, recording the echo of the sound pulse from the actual material filling level and measuring, as a measure of the filling level, the time interval between the end of the transmitted pulse and the end of the echo pulse.

Another object of the invention is to provide a device for measuring the height of filling material on a surface, which comprises a surface over which the filling material is accumulated to an actual filling level, transmitting and receiving means located in a fixed position over the surface for transmitting and receiving a sound pulse of a duration at least equal to the time required to travel to the surface and return and for also receiving the echo pulse which is returned, and measuring means connected to the transmitting and receiving means for measuring the time interval between the end of the transmitted pulse and the end of the echo pulse.

A further object of the invention is to provide a device for measuring the height of filling material on a surface which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference should be had to the accompanying drawings and descriptive matter in which there is illustrated a preferred embodiment of the invention.

DESCRIPTION OF THE PREFERRED EMBODIMENT

Figure 1:
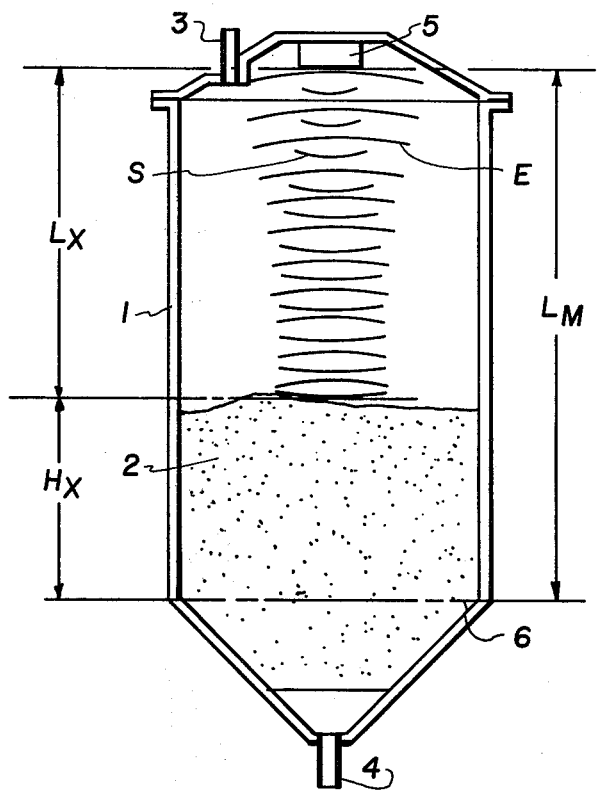
FIG. 1 is a diagrammatic representation of the measurement of the filling level in a container using the echo-sounding principle.

FIG. 1 is a diagrammatical sectional view showing a closed container 1, containing filled material 2, regarding which, it is assumed by way of example, that it concerns a granular loose material. The material may be filled into the container through a filling pipe 3 and may be removed from the container through a discharge pipe 4 mounted at the lowest point of the container.

To measure the filling level in the container, an electroacoustic transducer 5 is provided at the highest point, and when excited by an electric pulse generator, which has not been shown, it acts as a transmitter and produces a transmitted pulse S in the form of a sound wave or ultrasonic wave, propagated by the transducer 5 to the surface of the filled material 2. A fraction of the energy of the transmitted pulse is reflected on the filled material surface and is returned as echo pulse E to the transducer 5 which then acts as a receiver. A time-measuring arrangement (not shown) is connected to transducer 5 and measures the total transit time from the commencement of the transmission of the transmitted pulse S to the commencement of the reception of the echo pulse E. This total transit time is obviously twice as long as the single transit time from the commencement of the transmission of the transmitted pulse S to the commencement of the reception of the echo pulse E. The speed of sound in the space above the filled material, which space is filled with gas, is known. It is thus possible to determine from the measured time the distance $L_x$ traveled by transmitted pulse to the surface of the filled material. On the other hand, the distance $L_M$ between the transducer 5 and the reference plane 6 (e.g., container bottom) corresponding to zero filling level is known. Consequently, the filling level $H_x$ to be measured can also be determined from the following relationship:

$$H_x = L_M - L_x.$$

Figure 2:
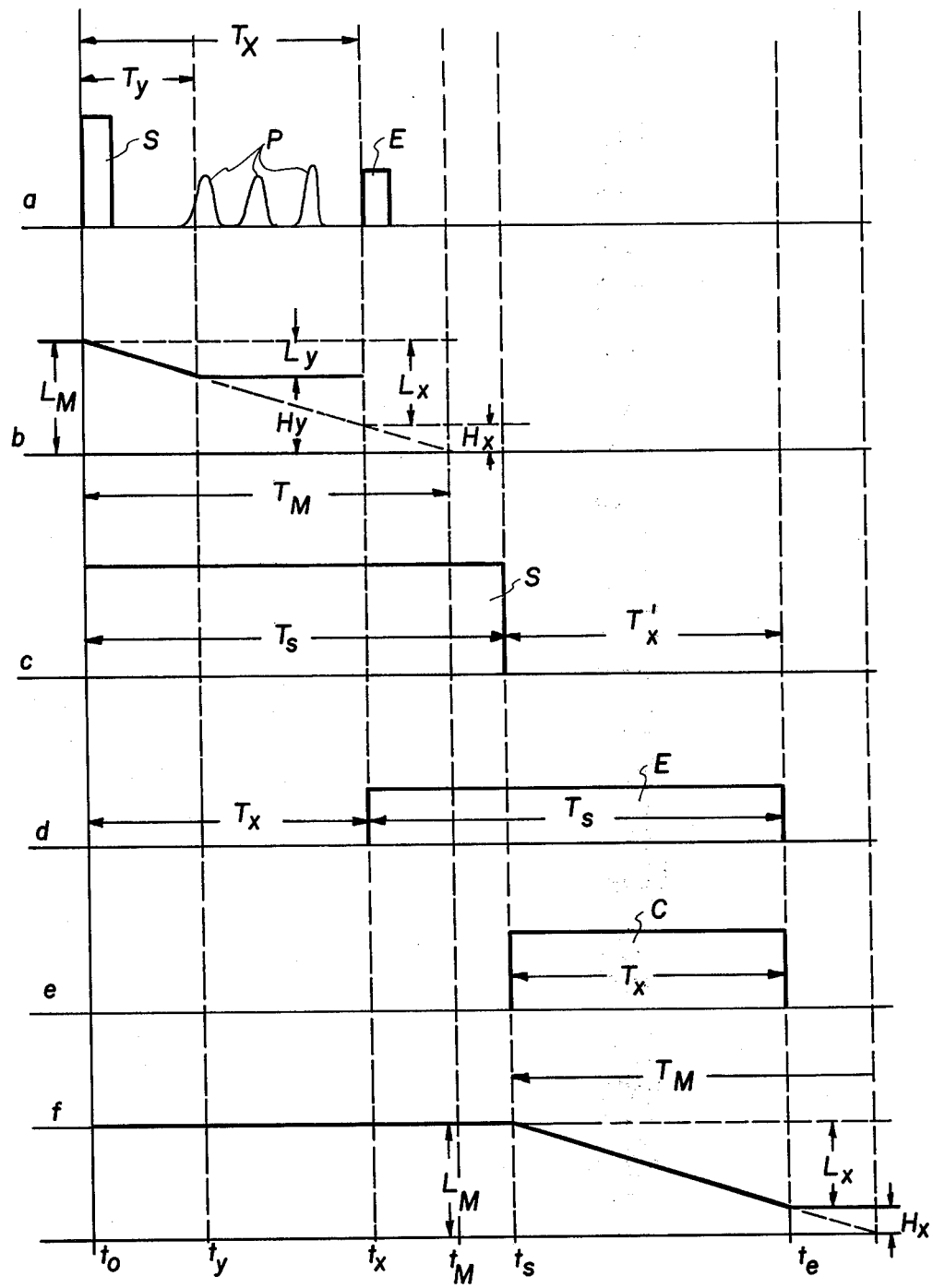
FIG. 2 shows diagrams which explain the known filling-level measurement with short pulses and the filling-level measurement by the method according to the invention.

The diagrams $a$ and $b$ of FIG. 2 represent the relationships occurring when the filling level measurement, shown in FIG. 1, is carried out with transmitted pulses whose duration is short compared with the transit time to be measured. As shown by the diagram $a$ of FIG. 2, the transmission of the transmitted pulse S commences at the point of time $t_o$, and the arrival of the echo pulse E at the transducer 5 commences at the point of time $t_x$. The time-measuring device should measure length of time $T_x$ proportional to the distance $L_x$. For this purpose, it is started by the commencement of the transmitted pulse S, and should be stopped by the commencement of the echo pulse E.

However, since the user wishes to measure the filling level $H_x$, and does not wish to measure the distance $L_x$, the time-measuring device before the commencement of measurement is preset to a value corresponding to the distance $L_M$. The time-measuring device is such that, after starting, it diminishes the indications from this initial value linearly at a speed that is so dimensioned that after a total transit time $T_M$, corresponding to the distance $L_M$, at the point of time $t_M$, the indicated value zero would be reached. This is represented in dash lines in diagram $b$ of FIG. 2. If the time-measuring device is stopped at the point of time $t_x$ by the echo pulse E, the indication will have been reduced by an amount corresponding to the distance $L_x$ and, therefore, the filling level $H_x$ is indicated directly.

This effect may be achieved, for example, by using a digital backward counter as the time-measuring device, which before the commencement of measurement, is set to an initial counting position corresponding to the distance $L_M$, and after starting, reduces its counting position by counting timing pulses of constant frequency. The same effect can also be obtained by means of an analogue store, comprising, for example, a capacitor, which before the commencement of measurement, is charged to an initial voltage and is discharged linearly after starting of the time-measuring device.

In this method, if interference pulses P of a strength and nature arrive such that they are processed as echo pulses, between the transmission of the transmitted pulse S and the reception of the echo pulse E at the receiving transducer, the time-measuring device is stopped at the point of time $t_y$ on the arrival of the first interference pulse P. It has then measured only a total transit time $T_y$ corresponding to a distance $L_y$ and, consequently, it indicates an incorrect filling level $H_y$.

This source of error is avoided by means of the method represented in diagrams $c$ to $f$ of FIG. 2. Diagram $c$ shows the transmitted pulse S transmitted in this method. The duration $T_S$ of this transmitted pulse is greater than the greatest occurring total transit time $T_x$. The transmitted pulse thus ends at a point of time $t_s$ situated after the point of time $t_M$.

The reception of the corresponding echo pulse E shown in diagram $d$, begins at the point of time $t_x$ after the total transit time $T_x$ corresponding to the filling level concerned. The echo pulse has of course the same duration $T_S$ as the transmitted pulse, and it terminates at a point of time $t_e$ situated at length of time $T'_x$ after the point of time $t_s$, corresponding to the end of the transmitted pulse. It will be readily apparent that the time interval $T'_x$ is exactly equal to the time interval $T_x$.

The time-measuring device is again such that from an initial condition corresponding to the distance $L_M$, its indications are diminished linearly (diagram $f$). In this case, however, at the end of the transmitted pulse at the point of time $t_s$, it is set in operation and is stopped at the point of time $t_e$ at the end of the echo pulse. The end position reached on stopping then corresponds exactly to the filling level $H_x$ to be measured.

For controlling the time-measuring device, there is preferably provided a control device generating a transmitted pulse C, see diagram $e$ of FIG. 2, which begins at the end of the transmitted pulse S and terminates at the end of the echo pulse E. The control pulse C thus has the duration $T_x$.

It will be readily apparent that interference pulses which occur during the duration of the transmitted pulse S have no influence whatsoever on the measurements, since no time measurement takes place during this time.

Interference pulses occurring during the time measurement between the points of time $t_s$ and $t_e$, cannot falsify the measured result because they are superimposed on the echo pulse only, but cannot simulate the end of the echo pulse which alone decides the end of the time measurement.

By steps taken to prevent restarting of the time measurement, interference pulses occurring after termination of the time measurement can be easily rendered ineffective.

The only source of error in this method is a lengthening of the time measurement by an interference pulse superimposed at the end of the echo pulse. However, the probability of the occurrence of such interference pulses is comparatively slight. Furthermore, the error caused thereby is minimal, since the duration of interference pulses is usually very short. Finally, in the method described, this source of error may also be precluded completely by imparting a modulation to the transmitted pulse and constructing the receiving devices such that they respond only to signals having the said modulation.

Figure 3:
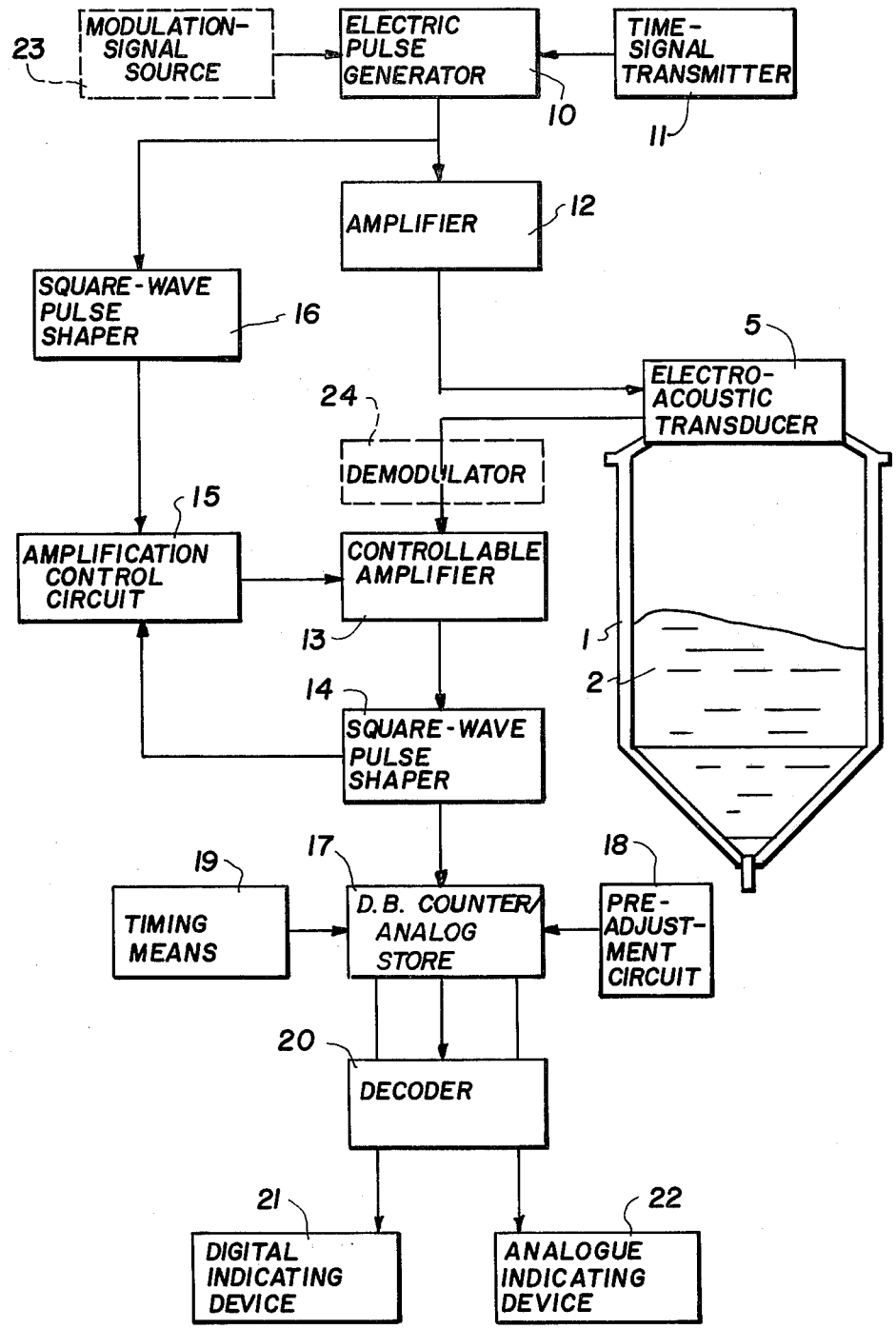
FIG. 3 shows the block circuit diagram of one embodiment of the arrangement, according to the invention.

FIG. 3 shows the block diagram of a circuit arrangement for carrying out the method described in the foregoing. This Figure again represents diagrammatically the container 1 with the filling material 2 and a transducer device 5. An electric generator 10 produces pulses with the desired frequency of the soundwave or ultrasonic wave. The duration of these pulses is determined by an adjustable time signal transmitter 11. The output of the pulse generator 10 is connected via an amplifier 12 to the transmitting transducer in the transducer arrangement 5 which therefore transmits into the container 1 a sound pulse or ultrasonic pulse which has the duration $T_S$, shown in diagram c of FIG. 2.

Echo pulse E which is received by the receiving transducer of transducer arrangement 5, is fed to an amplifier 13 with controllable amplification, to whose output a square-wave pulse shaper 14 is connected. The amplification control input of the controllable amplifier 13 is connected to an amplification control circuit 15 which is connected, on the one hand, via a square-wave pulse shaper 16 to the output of the pulse generator 10 and, on the other hand, to the square-wave pulse shaper 14.

The amplification control circuit 15 is such that for the duration of the square-wave pulse provided by the square-wave pulse shaper 16, that is to say, for the duration of the transmitted pulse S, the amplification of the amplifier 13 is kept to zero value or to a very small value, so that during this period, the amplifier 13 supplies practically no output signal. After the end of the transmitted signal S, i.e., at the point of time $t_s$ of FIG. 2, the amplification control circuit 15 brings the amplification of amplifier 13 to a value sufficient for processing the echo pulse, so that amplifier 13 now supplies for the duration of the echo pulse E an output signal which is brought by the square-wave pulse shaper 14 into the shape of a square-wave pulse. This square-wave pulse terminates with the end of the echo pulse and thus corresponds to the control signal C, shown in diagram c of FIG. 2.

The square-wave pulse delivered by the square-wave pulse shaper 14 controls a digital backward counter 17 which is adjusted by a preadjustment circuit 18 to an initial counter position before each measurement, and for the duration of the square-wave pulse, counts backwardly, with constant following frequency, the time pulses given by a timing means 19.

A decoder 20 which supplies an output signal corresponding to the counter position at the time is connected to the stepped outputs of the backward counter 17. This output signal may be indicated in a digital indicating device 21 or in an analogue indicating device 22, and after the stoppage of the backward counter 17 indicates directly the filling level $H_x$ to be measured, as follows from diagram f of FIG. 2.

In order to adapt this circuit to containers 1 of different heights, it is only necessary to adjust the duration of the transmitted pulse in the time-signal transmitter 11 and the initial counter position in the preadjustment circuit 18, in accordance with the longest transit time occurring.

This circuit may be modified by replacement of the digital backward counter 17 by an analogue store comprising a capacitor, to which an initial charge is applied before the commencement of measurement, and which is discharged linearly for the duration of the square-wave pulse delivered by the square-wave pulse shaper 14. The capacitor voltage attained at the end of the time measurement may be indicated directly in an analogue indicating device. If a digital indication is desired, an analogue-digital converter is connected to the analogue store.

A further advantageous form of the circuit arrangement of FIG. 3 is to impart a modulation to the transmitted pulses and to develop the receiving arrangement such that it responds only to received signals having this modulation. For this purpose, the pulse generator 10 may be controlled by a modulation-signal source 23 indicated in dash lines in FIG. 3, and a demodulator 24, indicated in dash lines, may be connected in front of the amplifier 13. Amplification control circuit 15 is then of a type that selectively responds to modulation. The modulation may be an amplitude modulation or a frequency modulation.

The application of frequency modulation affords additional possibilities. Thus, for example, the end of the transmitted pulse may be marked by a variation in modulation, so that the unavoidable after-oscillation of the transducer is disregarded during the measurement. Accurate recognition of the duration of the transmitted pulse and the duration of the echo pulse is also possible by frequency modulation of a lengthy wave pulse of this kind. This, in its turn, means that by suitable electronics, the intermediate analogue step of evaluation may be omitted, and a digital evaluation may be carried out directly, which again implies a reduction in the interference sensitivity of, for example, a device according to this working method. Such direct digital counting also gives average values automatically.

A further advantage of such modulation of the wave pulse is to be seen in the fact that by means of a simple phase recognition, the coarse measurement may be divided more finely into individual digital sections.

Furthermore, the transmission of a long wave pulse makes it possible to use the Doppler effect for recognizing the frequency shift of echoes reflected as distrubing pulses by the falling filling material. It is thereby possible to differentiate between the useful echo reflected by the surface of the material and interference echoes.

While a specific embodiment of the invention has been shown and described in detail to illustrate the application of the principles of the invention, it will be understood that the invention may be embodied otherwise without departing from such principles.

What is claimed is:

1. A method of measuring the level of filling material on a surface, comprising transmitting a sound pulse toward the filling material level, the sound pulse having a duration equal to at least the time it would take the sound pulse to travel to the lowermost level of the material on the surface, recording the echo of the sound pulse coming from the actual material filling level, and measuring, as a measure of the filling level, the time interval between the end of the transmitted pulse and the end of the echo pulse.

2. A method of measuring the height of filling material on a surface, according to claim 1, wherein said transmitted pulse is frequency modulated.

3. A device for measuring the height of filling material on a surface, comprising a surface over which filling material is accumulated to an actual filling level, transmitting and receiving means located in a fixed position over said surface for transmitting and receiving a sound pulse of a duration at least equal to the time required to travel to the surface and return and for receiving the echo pulse which is returned, and measuring means connected between said transmitting and receiving means for measuring the time interval between the end of the transmitted pulse and the end of the echo pulse.

4. A device for measuring the height of filling material on a surface, according to claim 2, wherein said transmitting and receiving means include an electroacoustic transmitting and receiving transducer, an electric pulse generator exciting said transducer, said measuring means being connected to the output of said electroacoustic transmitting and receiving transducer, said electroacoustic transmitting and receiving transducer being mounted above said surface, said measuring means including a time-measuring device and a control circuit connected to said time-measuring device for starting the time-measuring device at the end of the transmitted pulse and stopping it at the end of the echo pulse.

5. A device for measuring the height of filling material on a surface, according to claim 4, wherein said time-measuring device comprises a digital backward counter, means for adjusting said counter to an initial counter position before each measurement, said backward counter being started and terminated by said control circuit.

6. A device for measuring the height of filling material on a surface, according to claim 5, wherein said initial counter position is so selected that the backward counter reaches the zero counter stage in the maximum total transit time corresponding to the lowermost filling level.

7. A device for measuring the height of filling material on a surface, according to claim 5, wherein said initial counter position is adjustable.

8. A device for measuring the height of filling material on a surface, according to claim 4, wherein said time-measuring device comprises an analogue store, means for charging said store to an initial charge before each measurement, the discharge of said store being initiated and terminated by said control circuit.

9. A device for measuring the height of filling material on a surface, according to claim 8, wherein the initial charge is such that the analogue store is completely discharged in the maximum total transit time corresponding to the empty container.

10. A device for measuring the height of filling material on a surface, according to claim 8, in which the initial charge is adjustable.

11. A device for measuring the height of filling material on a surface, according to claim 4, wherein said control circuit comprises an amplifier connected to said transducer having a controllable amplification factor and an amplification control circuit for keeping the amplification factor of the amplifier for the period of the transmitted pulse at zero value or at a very small value and maintaining it at a greater value for the duration of the echo pulse.

12. A device for measuring the height of filling material on a surface, according to claim 11, wherein said transmitted pulse is modulated and said amplification control circuit is such that it responds selectively to modulation.

13. A device for measuring the height of filling material on a surface, according to claim 12, wherein said transmitted pulse is frequency modulated.

* * * * *